United States Patent
Abraham

(12) 
(10) Patent No.: US 6,586,417 B1
(45) Date of Patent: Jul. 1, 2003

(54) ESTER AND ETHER DERIVATIVES OF 4-HYDROXY 4-ANDROSTENE-3,17-DIONE AND A METHOD FOR THE REGULATION OF ATHLETIC FUNCTION IN HUMANS

(75) Inventor: Sal Abraham, Dunmore, PA (US)

(73) Assignee: NutriSport Pharmacal, Inc., Franklin, NJ (US)

( * ) Notice: Subject to any disclaimer, the term of this patent is extended or adjusted under 35 U.S.C. 154(b) by 0 days.

(21) Appl. No.: 10/063,415

(22) Filed: Apr. 22, 2002

(51) Int. Cl.$^7$ ............................................... A61K 31/56
(52) U.S. Cl. ........................................................ 514/178
(58) Field of Search ......................................... 514/178

(56) References Cited

U.S. PATENT DOCUMENTS

| | | |
|---|---|---|
| 4,235,893 A | 11/1980 | Brodie |
| 5,861,389 A | 1/1999 | Rademaier |
| 5,880,117 A | 3/1999 | Arnold |
| 6,242,436 B1 | 6/2001 | Llewellyn |

OTHER PUBLICATIONS

Lescherber, G. et al. Influence of an aromatase inhibitor (4–acetoxy–4–androstene–3,17–dione) on experimentally induced impairment of spermatogenesis in immature rats, Journal article, Andrologia 1989 Nov.–Dec.;21(6):529–34, Blackwell Publishing, Germany, West.

Evans, G. et al. Effect of an aromatase inhibitor (4–acetoxy–4–androstene–3,17–dione) on the stimulatory action of luteinizing hormone on estradiol–17 beta synthesis by rat preovulatory follicles in vitro. Journal article, Biol Reprod. 1981 Sep.;25(2):290–4, High Wire Press, United States.

Gardi, R. et al. New classes of orally active hormonal derivatives. II. 17–Cycloalk–1'–enyl ethers of 17–hydroxy–androstanes and 19–norandrostanes. Journal article, Steroids May 1972 19:5 639–47, Elsevier Science, United States.

Davies, JH. et al. Effects of 4–hydroxyandrost–4–ene–3, 17–dione and its metabolites on 5 alpha–reductase activity and the androgen receptor. Journal article, J. Enzyme Inhib 1992 6:2 141–7, Taylor and Francis Health Sciences Switzerland.

Marsh, DA. et al. Synthesis of deuterium– and tritium–labelled 4–hydroxyandrostene–3,17–dione, an aromatase inhibitor, and its metabolism in vitro and in vivo in the rat. Journal article, Biochem Pharmacol. Mar. 1982 1;31(5):701–5. Elsevier Science, England.

Waxman, DJ. et al. P450–catalyzed steroid hydroxylation: assay and product identification by thin–layer chromatography. Journal article, Methods Enzymol 1991 206:462–76 Academic Press, united States.

*Primary Examiner*—Rebecca Cook

(57) ABSTRACT

This invention relates to a method of administering an effective amount of at least one of the ester or ether derivatives of 4-hydroxy 4-androstenedione for the regulation of athletic function in humans.

7 Claims, No Drawings

ESTER AND ETHER DERIVATIVES OF 4-HYDROXY 4-ANDROSTENE-3,17-DIONE AND A METHOD FOR THE REGULATION OF ATHLETIC FUNCTION IN HUMANS

BACKGROUND OF INVENTION

This invention relates to the ester and ether derivatives of 4-hydroxy 4-androstenedione as a means of regulating athletic function in humans. In men, the normal balance of sex steroids is characterized by a greater amount of androgens over estrogens. When estrogen exceeds androgen levels in males a cascade of detrimental effects can take place for instance, decreased sperm count, low free testosterone levels, decreased muscle mass and decreased strength. When androgens are manipulated to exceed estrogen above the normal androgen to estrogen ratio the exact opposite takes place with an emphasis on the promotion of lean body mass and strength to aid in enhancing physical performance.

The use of 4-hydroxy 4-androstenedione is intended to gradually increase androgen levels while simultaneously decreasing estrogen and dihydrotestosterone (DHT). Natural androgen production is increased by the stimulation of the hypothalamic pituitary axis via an increase in luteinizing hormone (LH) levels coupled by the direct stimulation of testosterone by 4-hydroxy 4-androstenedione. Luteinizing hormone (LH) is responsible for the production of total serum testosterone and testicular function. This gradual increase in testosterone then decreases the amount of steroid hormone binding globulin (SHBG) which increases the amount of free or active testosterone. Testosterone and dihydrotestosterone (DHT) circulate in plasma either unbound (free approximately 2–3%) or bound to plasma proteins. The binding proteins include sex hormone-binding globulin (SHBG) and albumin. SHBG is a β-globulin that has a low capacity for steroids, but binds with high affinity. SHBG has its highest affinity for DHT and its lowest affinity for estradiol. In men, circulating testosterone is bound 44–65% to SHBG and 33–54% to albumin, whereas in women, testosterone is bound 66–78% to SHBG and 20–32% to albumin.

Serious and/or professional athletes are known to utilize intramuscular injection and/or peroral administration of pharmaceutical androgens for the promotion of muscle mass and athletic performance. Various testosterone esters in oil depot form have been utilized as intramuscular injection. These weekly injections of synthetic testosterone cause supraphysiological surges in androgen levels which then leave the body deficient in androgens until the next injection. These supraphysiological levels of testosterones readily convert to estrogen and dihydrotestosterone (DHT) which can lead to side effects such as gynocomastia and benign prostrate hypertrophy (BPH). Another negative side effect is the possible down regulation of the hypothalamic pituitary axis resulting in loss of natural testosterone production.

The oral route of synthetic androgen administration consists of testosterone derivatives that are 17 alpha-alkylated for enhanced oral bioavailability (i.e. Methyltestosterone). This alkylation allows the steroids to withstand the 17 beta-hydroxyl oxidation in the liver. This appears to alleviate the dosing and blood hormone problems as compared to injections but it can cause undue stress to the liver and increase the possibility of hepatotoxicity.

Pharmaceutical anti-estrogens have also been utilized in an attempt to promote androgen accumulation. Theoretically the inhibition of estrogen absorption should shift the hormonal balance toward a predominant androgen ratio. Although this method of therapy is inadequate due to the mechanism of action that most anti-estrogens are based upon. Anti-estrogen drugs such as Tamoxifen act on the estrogen receptor and thus block or inhibit estrogen absorption. This receptor blockade inhibits absorption but it does not lower total circulating estrogen levels. These anti-estrogens also do not dictate the specific site of estrogen receptor inhibition in the body. Since the actual estrogen concentration has not decreased there is no signal sent to the hypothalamic-pituitary axis to increase androgen production.

U.S. Pat. No. 5,880,117 to Patrick Arnold, relates a method of using of using the oral precursor hormone 4-androstenediol as a means of increasing testosterone levels in humans. This hormone represents an improvement in standard therapies, since 4-androstenediol does not seem to be open to aromatase in its initial state. The possibility that this compound will convert to an estrogen over an androgen is chemically unlikely. The end product testosterone however is still readily aromatized. The compound suggested in this patent does offer advantages over standard therapies in that the compound in question avoids a direct path of estrogen conversion and provides a less toxic peroral route of administration. The target hormone of replacement may still be less than ideal due to it's conversion to estrogen and dihydrotestosterone (DHT).

U.S. Pat. No. 6,242,436 to William Llewellyn, relates a method of using the oral precursor hormones 5alpha-androstanediol or 5alpha-androstanedione as a means of increasing dihydrotestosterone levels in humans. Dihydrotestosterone (DHT) is a more potent form of testosterone, shown to be roughly three to four times more active in the human body in comparison. This hormone represents an improvement, since 5alpha-androstanediol or 5alpha-androstanedione are natural, non-toxic, and quickly metabolized to active form after oral administration and unable to be aromatized into estrogens due to their structure. The compound suggested in this patent does offer advantages over standard therapies in that the compound in question avoids a direct path of estrogen conversion and provides a less toxic peroral route of administration. However, dihydrotestosterone (DHT) is not the most ideal form of testosterone due to it's causative relationship with benign prostrate hypertrophy (BPH) and other androgenic side effects.

U.S. Pat. No. 5,861,389 to Radlmaier, et al. discloses a method of increasing androgen levels in males by administering various aromatase inhibitors including atamestane, formestane, pentrozole, arimidex, fadrozole, and vorozole. These compounds block the aromatase enzyme which is responsible for the conversion of androgen to estrogens. Long term studies with aromatase inhibitor atamestane clearly demonstrates the restoration of androgens over estrogens at 24 and 48 weeks respectively. The method of this invention dictates the gradual decrease in estrogen blood concentration, which produces a signal to increase natural androgen production. This hormonal signal results in increased total and free androgen concentrations. This invention is an improvement over the standard exogenous administration of synthetic androgens for male androgen deficiency. These improvements include an inability to shut down the hypothalamic-pituitary axis, provide a safer oral route and not cause a supraphysiological surge in androgen concentrations.

SUMMARY OF INVENTION

The use of illicit synthetic exogenous testosterone for the promotion of muscle mass and work performance is well known throughout athletic circles. However these therapies, besides being illegal, result in the aromatization of the target hormone and put undue stress upon the liver. Dietary supplement manufactures have attempted to correct these problems by the use of pro-hormones for the promotion of physical performance. For instance, U.S. Pat. Nos. 5,880,117 and 6,242,436 attempt to correct some of these problems by the peroral administration of androgen precursors. Now while the active androgen precursor is unable to aromatize, the target hormone of U.S. Pat. No. 5,880,117 can produce substantial conversion to estrogen and dihydrotestosterone (DHT) while the target hormone of U.S. Pat. No. 6,242,436 is directly converted to dihydrotestosterone (DHT). The problem of the present invention is to provide a compound that gradually increases androgen levels for the promotion of fat free mass and athletic performance without causing aromatization, hepatotoxicity, or supraphysiological surges in androgen blood concentrations. According to the invention these problems are solved by the use of the steroidal aromatase inhibitor 4-hydroxy-4-androstenedione. The use of this compound causes a gradual decline in estrogen levels which produces a signal to the hypothalamic-pituitary axis in order to gradually increase androgen levels and directly stimulate total and free testosterone production for the promotion lean body mass and physical performance with none of the previous mentioned negative side effects. 4-hydroxy-4-androstenedione is a naturally occurring compound that can sold as dietary supplement. The ester and ether analogs of this compound can also be sold as a dietary supplement as long as the ester and ether additions are utilized for increasing oral bioavailability.

DETAILED DESCRIPTION

The chemical term 4-hydroxy 4-androstenedione refers to the isomer: 4-hydroxy 4-androstene-3, 17-dione. 4-hydroxy 4-androstenedione (Formestane), is an analog or derivative of the naturally occurring precursor hormone 4-androstenedione. Viable chemical esters of this compound include methyl, ethyl, propyl, butyl, and cyclohexyl carbonate as well as, acetate, heptanoate, decanoate, hemisuccinate, and benzoate. Viable chemical ethers include tetrahydropyranyl (THP), cyclopentyl (CPT), cyclohexyl and tetrahydrofuranyl (THF) ethers. This invention concerns the esters and ethers of the main isomer form of 4-hydroxy 4-androstene-3, 17-dione.

The mechanism of estrogen biosynthesis has been thoroughly reviewed and thus has lead to the development of numerous compounds that inhibit androgen to estrogen conversion. It is believed that the inhibition of estrogen biosynthesis is controlled by the availability of the aromatase enzyme which converts androgens to estrogens. Steroidal aromatase inhibitors are a class of compounds that have been successfully utilized to increase androgen levels in males and represent significant improvement in standard androgen deficiency therapies. Some of these compounds include androsta-4,6-diene-3,17-dione, androsta-4,6-dien-17.beta.-ol-3-one acetate, androsta-1,4,6-triene-3,17-dione, 4-androstene-19-chloro-3,17-dione, 4-androstene-3,6,17-trione that are described by Schwarzel W, Kruggle W, Brodie H, (Endocrinology) 1973, Vol. 92, No. 3, page 866–880. 4-Hydroxy 4-androstenedione is yet another improvement over standard dietary androgen supplements due to its ability to increase androgen levels while simultaneously decreasing estrogen and dihydrotestosterone (DHT).

Animal tests carried out by Leschber G, Nishino Y, Neumann F (Andrologia) Nov.–Dec. 21, 1998(6):529–34 has demonstrated 4-acetoxy-4-androstenedione's (4-hydroxy 4-androstenedione acetate) ability to increase androgen production via the stimulation of luteinizing hormone. Subcutaneous treatment in rats with 19-hydroxytestosterone produced a decrease in weight of the testis, ventral prostrate, seminal vesicle and luteinizing hormone levels. Researchers noted that the effects of 19-hydroxytestosterone where similar to that of estradiol. Administration of 4-acetoxy-4-androstenedione restored meiotic activity, increased the weight of the genital organs, and increased luteinizing hormone (LH) levels. Researchers then suggested that these results indicate that 4-acetoxy-4-androstenedione might be suitable for the treatment of estrogen induced infertility in human males.

Previous in vitro animal studies carried out by Evans G, Leung P C, Brodie A M, Armstrong D T (Biol Reprod) Sep. 25, 1981(2):290–4 have demonstrated 4-acetoxy-4-androstenedione's ability to directly stimulate testosterone whether in the presence of luteinizing hormone (LH) or not. Researchers examined the effects of placebo, luteinizing hormone (LH), 4-acetoxy-4-androstenedione, and luteinizing hormone (LH) plus 4-acetoxy-4-androstenedione on rat follicles in vitro. In regards to testosterone, they found that within the first eight hours 4-acetoxy-4-androstenedione had the ability to directly stimulate testosterone alone and greatly stimulate testosterone in combination with luteinizing hormone (LH). Interestingly enough within the next sixteen hours they discovered 4-acetoxy-4-androstenedione alone was stimulating testosterone three times as much as luteinizing hormone (LH) while the combination also continued to stimulate testosterone.

4-Acetoxy-4-androstenediones ability to decrease dihydrotestosterone (DHT) was demonstrated by Mott M, Zoppi S, Brodie A M, Martini L (J Steroid Biochem) Oct. 25, 1986(4):593–600. Researchers studied the effects of 1,4,6-androstatriene-3,17-dione (ATD), 4-hydroxy-4-androstenedione (4-OH-A), and 4-acetoxy-4-androstenedione (4-Ac-A) on the metabolism of testosterone, dihydrotestosterone, and androstenedione in the ventral prostrate of the adult male rat. Researchers found that that 4-OH-A and 4-Ac-A were able to inhibit the transformation of testosterone to dihydrotestosterone in the ventral prostrate. This site specific dihydrotestosterone inhibition demonstrates an improvement over standard therapies and other steroidal aromatase inhibitors due to dihydrotestosterones causative relationship with benign prostrate hypertrophy (BPH).

The chemical addition of esters and ethers to 4-hydroxy 4-androstenedione are designed to enhance stability and oral bioavailability. The chemical addition of various ethers to the hydroxyl portion of the molecule, such as tetrahydropyranyl, cyclopentyl, cyclohexyl or tetrahydrofuranyl ether, enables the compound to become lipophilic or fat soluble. This lipophilicity allows the compound to be absorbed via the lymphatic system and bypass the first-pass through the liver allowing more of the active compound to enter the bloodstream as described by Gardi R, Falconi G, Pedrali C, Vitali R, Ercoli A (Steroids) May 19, 1972:639–47. Although, the base compound 4-hydroxy 4-androstenedione has been shown to exhibit adequate oral absorption by Dowsett M, Goss P E, Powles T J, Hutchinson G, Brodie A M, Jeffcoate S L, Coombes R C (Cancer Res) Apr. 1, 1987;47(7):1957–61. Researchers noted that similar estrogen suppression was achieved by a single i.m. injection of 125 mg of 4-hydroxy 4-androstenedione and by 500 mg of 4-hydroxy 4-androstenedione p.o. (by mouth) daily after 1 week, but escape from suppression was more rapid.

4-Hydroxy 4-androstenedione is steroidal aromatase inhibitor that inhibits estrogen biosynthesis, stimulates natural production of total and free testosterone, and may inhibit DHT formation in the prostrate. It does this by directly stimulating testosterone production and by inhibiting the Cytochrome P-450 enzyme which converts testosterone to estrogen. Once estrogen levels fall a signal is sent to the hypothalamic pituitary axis to produce (LH) luteinizing hormone and decrease (SHBG) steroid hormone binding globulin. LH then stimulates the testes to increase total testosterone production, in which a large portion is free or active testosterone due to the decrease in SHBG. This increased amount of testosterone is then metabolized with less estrogen and DHT conversion. The total estrogen conversion is decreased by the aromatase mechanism, while the DHT inhibition is localized in the prostrate. It appears that the 5-alpha reductase isoenzymes in the prostrate are inhibited resulting in less DHT formation from testosterone.

Increases in lean body mass, strength, and work performance are predominately associated with the amount of free or active testosterone available in the body. These increases contribute to the regulation of athletic function and thus lead to enhanced physical performance. The ester and ether derivatives of 4-hydroxy-4-androstenedione have been shown to increase the natural production total and free testosterone with none of previously mentioned negative side effects associated with increases in androgen production. Thus the said compound can be given to humans either in conjunction with or without a high protein diet (1.25 to 1.8 grams protein/kilogram of body weight) and proper anaerobic training program in order to increase the variables associated with athletic function for the purpose of enhancing physical performance. Therefore this compound represents an improvement in standard dietary androgen supplementation for the regulation of athletic performance.

After an extensive review of the scientific literature and previous patents regarding the ability of steroidal aromatase inhibitors to decrease estrogen and increase total and free testosterone, it then became the focus of this invention that the esters and ethers of 4-hydroxy-4-androstenedione could be administrated perorally as an effective means of enhancing physical performance in humans. The oral daily doses can be between 20 to 1000 mg., but preferably 100 to 600 mg. The preferred daily dosing schedule should be divided into 3–6 sub dose applications per day in order maintain adequate blood hormone concentrations. In addition to per-oral use, the esters and ethers of 4-hydroxy-4-androstenedione can be effectively administered by several other routes including transdermal, sublingual, and intranasal.

What is claimed is:

1. A method of enhancing physical performance in a human in need thereof by administration to said human an effective amount of at least one of the ester or ether derivatives of 4-hydroxy-4-androstenedione.

2. The method of claim 1, wherein said ester or ether derivative of 4-hydroxy-4-adrostenedione is an ester or ether derivative of 4-hydroxy-4-androstene-3, 17-dione.

3. A method of claim 1, wherein said ester derivatives are selected from the group consisting of acetate, heptanoate, decanoate, hemisuccinate, benzoate, propionate, and carbonate.

4. A method of claim 1, wherein said ether derivatives are selected from the group consisting of tetrahydropyranyl, tetrahydrofuranyl, cyclopentyl, and cyclohexyl.

5. A method of claim 1, wherein said administration is peroral.

6. A method of claim 1, wherein said administration is selected from the group consisting of transdermal, sublingual, and intranasal.

7. A method of claim 1, wherein said effective amount is a daily dosage of 10 mg to 2000 mg.

\* \* \* \* \*